United States Patent [19]

Toso et al.

[11] Patent Number: 5,282,832
[45] Date of Patent: Feb. 1, 1994

[54] SUTURE CLIP

[75] Inventors: Kenneth E. Toso, Portchester, N.Y.; Michael S. Kolesa, Norwalk, Conn.

[73] Assignee: United States Surgical Corporation, Norwalk, Conn.

[21] Appl. No.: 959,060

[22] Filed: Oct. 9, 1992

[51] Int. Cl.⁵ .............................................. A61B 17/00
[52] U.S. Cl. ................................... 606/232; 606/151; 24/587
[58] Field of Search ................ 606/232, 151; 411/508, 411/913, 338; 24/453, 587, 662

[56] References Cited

U.S. PATENT DOCUMENTS

| D. 190,787 | 6/1961 | Schneider . | |
|---|---|---|---|
| D. 234,204 | 1/1975 | Miller et al. . | |
| 600,887 | 3/1898 | Pettit . | |
| 3,698,681 | 10/1972 | Lacey . | |
| 3,753,438 | 8/1973 | Wood et al. . | |
| 3,803,670 | 4/1974 | Johnson | 411/508 |
| 3,854,482 | 12/1974 | Laugherty et al. . | |
| 3,857,396 | 12/1974 | Hardwick . | |
| 3,896,527 | 7/1975 | Miller et al. . | |
| 3,910,281 | 10/1975 | Kietschka et al. . | |
| 3,976,079 | 8/1976 | Samuels et al. . | |
| 4,291,698 | 9/1981 | Fuchs et al. . | |
| 4,382,453 | 5/1983 | Bujan et al. . | |
| 4,387,489 | 6/1983 | Dudek | 24/133 |
| 4,470,737 | 9/1984 | Wollar | 411/508 |
| 4,492,232 | 1/1985 | Green . | |
| 4,498,476 | 2/1985 | Cerwin et al. . | |
| 4,519,392 | 5/1985 | Lingua . | |
| 4,536,924 | 8/1985 | Willoughby . | |
| 4,556,058 | 12/1985 | Green . | |
| 4,557,263 | 12/1985 | Green . | |
| 4,569,346 | 2/1986 | Poirier . | |
| 4,579,473 | 4/1986 | Brugger | 24/453 |
| 4,620,541 | 11/1986 | Gertzman et al. . | |
| 4,623,102 | 11/1986 | Hough, Jr. . | |
| 4,750,492 | 6/1988 | Jacobs . | |
| 4,866,818 | 9/1989 | Thompson . | |
| 4,969,892 | 11/1990 | Burton et al. | 606/218 |
| 5,078,731 | 1/1992 | Hayhurst | 606/232 |
| 5,143,500 | 9/1992 | Schuring | 411/913 |
| 5,160,339 | 11/1992 | Chen et al. | 606/158 |
| 5,171,251 | 12/1992 | Bregen et al. | 606/151 |

OTHER PUBLICATIONS

"A Technique for Suturing Soft Viscera Using Compression Sutures", Surgery, Gynecology & Obstetrics, O. Drew Grice, M.D., F.A.C.S., Dec. 1988, vol. 167.
Schaefer, M. D., et al., *Absorbable Ligating Clips*, Surgery, Gynecology & Obstetrics, vol. 154, pp. 513–516, (Apr. 1982).

*Primary Examiner*—Peter A. Aschenbrenner
*Assistant Examiner*—Gary Jackson

[57] ABSTRACT

A suture fastening device which includes a first member having a base and two resilient elongated legs extending from the base. The legs are provided with barbs for snap fit engagement with an aperture in a second member, i.e., a retainer. The suture is held in serpentine fashion by positioning the suture transversely across both the legs and then locking the first member and the retainer.

20 Claims, 3 Drawing Sheets

SUTURE CLIP

BACKGROUND OF THE INVENTION

1. Field of the Invention

The present invention relates to a fastening device for use in surgical procedures to secure a suture.

2. Background of the Art

Sutures are commonly used to close incisions and to reunite damaged tissue. Typically, the sutures are passed through the tissue and the free ends of the sutures are tied together. In many instances, the suturing site is exposed to an extent sufficient to permit the surgeon to quickly tie the suture by hand. However, in some procedures such as arthroscopic, laparoscopic or endoscopic surgery, the suturing site is inaccessible by hand. As a result, the surgeon is usually required to tie the suture ends into a knot at a location remote from the suture site, and then manipulate suitably configured instruments for sliding the knot to the site.

For example, arthroscopic surgical procedures usually employ a small diameter cannula that extends through a small incision made in a joint. The sutures extend from the suturing site through the cannula. The exposed free ends of the sutures are tied by the surgeon and the knot is slid through the cannula to the suturing site.

Likewise, laparoscopic or endoscopic surgery also relies on small diameter cannulas to insert through small incisions in body tissue to gain access to the interior of the body. The operating instruments have relatively long and narrow portions which are inserted through a cannula to perform the operation in the interior of the body. The instrumentation for such procedures is actuated from outside the body. It can readily be understood that the dexterity required to free suture ends under such conditions not only places a burden upon the operating personnel, but also poses a greater risk to the patient.

Various devices are known which attempt to deal with the aforementioned problem.

For example, U.S. Pat. No. 5,078,731 to Hayhurst discloses a suture clip for engaging one or more suture thread lines. The Hayhurst suture clip, in an open position, is slidable along the suture(s). When positioned at the suturing site, the Hayhurst clip may then be closed to fix the position of the clip, thereby securing the suture(s).

U.S. Pat. No. 4,291,698 to Fuchs et al. discloses a button type suture retainer including a disk having a slot which extends to a passage for guiding a suture thread therethrough within the circumference of the disk. The passage is sealed by a clamping device for clamping a thread in the passage. The clamping device includes a disk segment movable parallel with the disk over the slot and passage to a latched position where its inner marginal part is past the passage, thereby bending the thread and holding it by friction and compression.

Other suture fixation devices are disclosed in U.S. Pat. Nos. 3,753,438; 3,857,396; 3,910,281; 3,976,079; 4,387,489; 4,750,492; and 4,969,892.

While the aforementioned devices perform the function of suture retention, there is yet need for an improved suture retainer clip which is simple in construction, easy to apply, and usable in laparoscopic or endoscopic or arthroscopic applications as well as in conventional surgical procedures.

SUMMARY OF THE INVENTION

A suture fastening device is provided herein which comprises a first member having a lengthwise extension defined by its longest side and including a base portion, first and second legs projecting from the base portion and extending lengthwise thereon, the first and second legs being resiliently biased toward a spaced apart position from each other and movable toward each other in response to force applied thereto; and a second member having a lengthwise extension defined by its longest side, the second member having an aperture for receiving said first and second legs of the first member. Preferably, the first and second legs are substantially perpendicular to said base member and substantially parallel to each other. In a preferred embodiment the first and second legs each possess a camming surface and the second member possesses camming means, such as an edge or surface for camming against these camming surfaces to move the first and second legs toward each other.

Another preferred feature of the present invention is the snap-fit locking engagement of the first and second members enabled by at least one barb extending from at least one of the legs, the barb having an abutment surface for preventing disengagement of said first and second members after they have been engaged.

The suture fastening device may be fabricated from a bioabsorbable material.

Also provided herein is a method for fastening a suture using the suture fastening device of the present invention by positioning one or more suture threads transversely across both the first and second legs, then locking together the first and second members, while placing the suture into a serpentine path. The flexure of the two legs will accommodate a range of suture sizes to be retained. When the suture is placed in tension, friction is developed at each of the multiple bends that the suture has been subjected to resulting in substantially higher retentive forces.

DETAILED DESCRIPTION OF PREFERRED EMBODIMENT(S)

Figure 1:
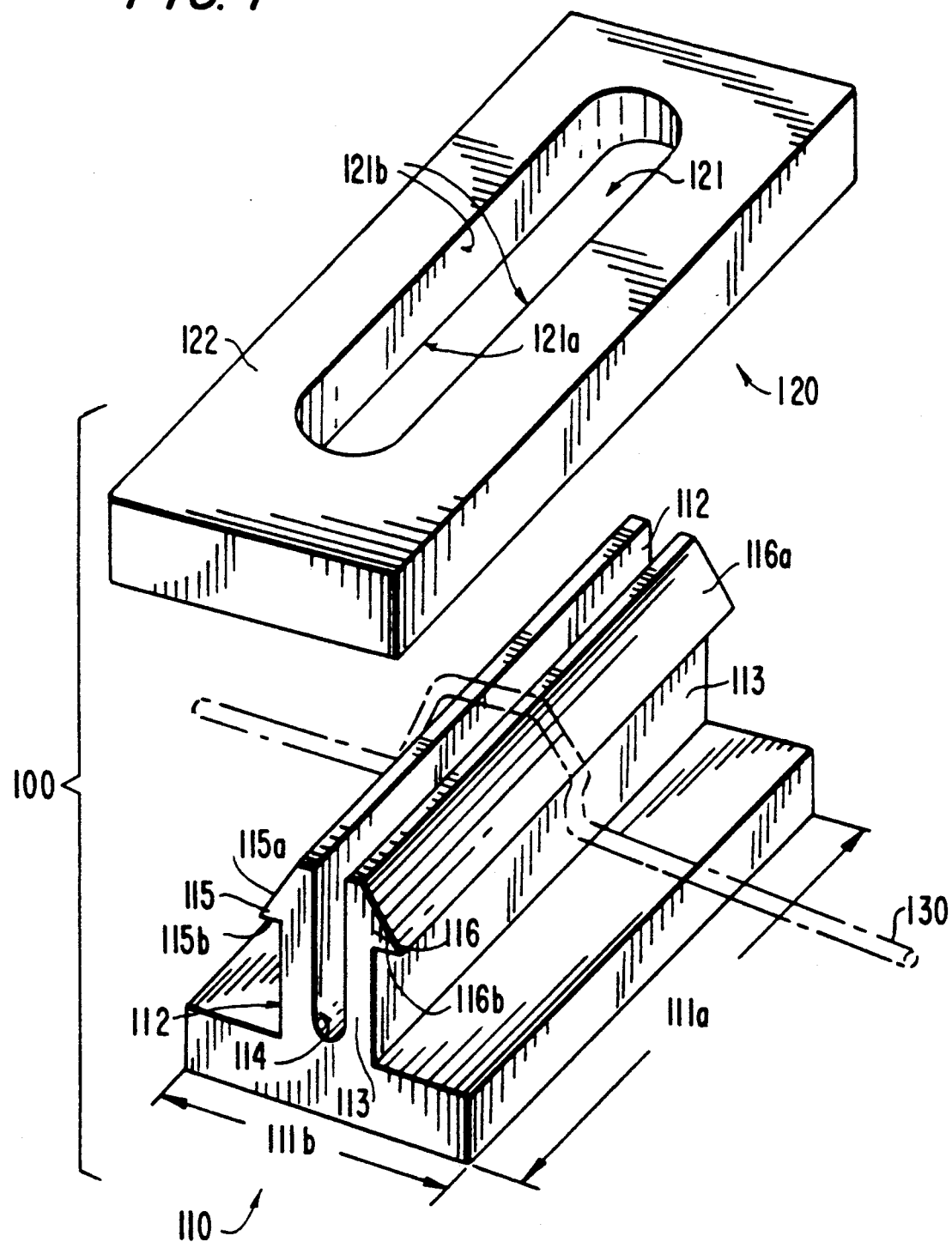
FIG. 1 is an exploded perspective view of the suture clip of the present invention.

Referring to FIG. 1, the suture clip of the present invention 100 preferably comprises two separable portions: a first portion 110 and a second portion 120 which snap together in interlocking engagement.

Each portion, 100 and 120, is preferably of integral construction and may be fabricated from any suitable polymeric material. Especially preferred are bioabsorbable polymeric material such as polymers and copolymers of glycolide, lactide, caprolactone and 1,4-dioxanone. The first member 110 includes a base 111 of generally rectangular shape having a lengthwise extension 111a longer than its width 111b. Projecting perpendicularly from base 111 are two legs 112 and 113. Legs 112 and 112 are spaced apart from each other thereby defining a gap 114 between them. Legs 112 and 113 extend lengthwise along the base and possess sufficient resiliency to be bent inwardly towards each other in response to force applied thereto when the first and second members 110 and 120 are assembled. The resiliency biases the first and second legs 112 and 113 to their original position.

Each leg 112 and 113 includes a locking barb, 115 and 116, respectively. The locking barbs 115 and 116 each have a camming surface, 115a and 116a respectively, and abutment surfaces 115b and 116b respectively, to facilitate snap fit engagement with the second member, i.e., retainer 120.

Figure 2:
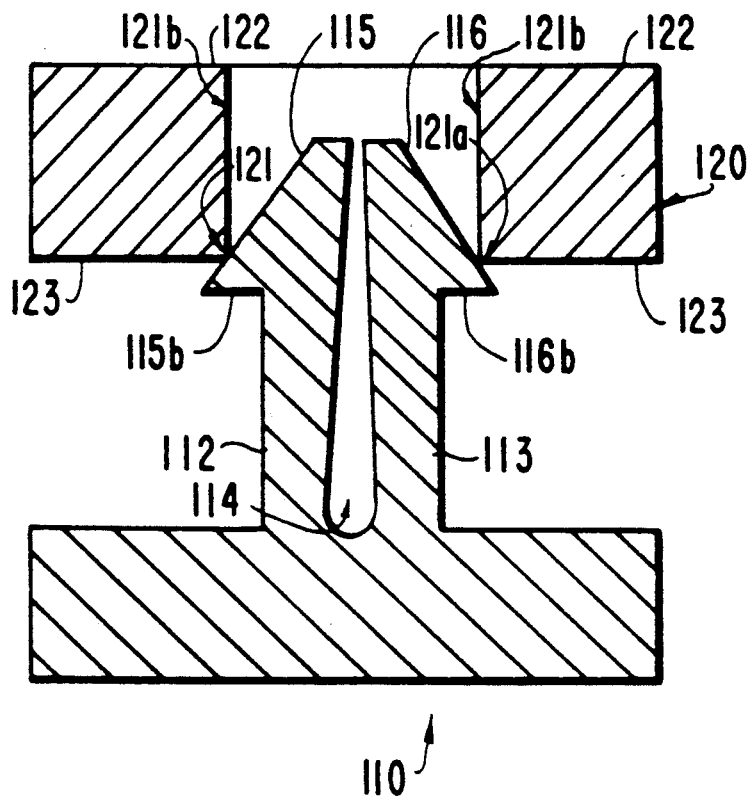
FIG. 2 is a sectional view showing the camming of the suture contacting legs during engagement with the retainer member.

Referring to FIGS. 1 and 2, retainer member 120 includes a top surface 122, a bottom surface 123, and a lengthwise extending aperture 121 configured and dimensioned to receive legs 112 and 113. The aperture 121 includes an edge 121a which cams against the camming surfaces 115a and 116a to move the upper portions of the legs 112 and 113 towards each other thereby permitting entry of barbs 115 and 116 through aperture 121 for snap-fit engagement of the first and second members 110 and 120. Aperture 121 also includes as a side wall 121b which acts as a capture surface, as explained below. Abutment surfaces 115b and 116b snap into a position wherein a force directed to cause separation of engaged members 110 and 120 will cause surfaces 115b and 116b to abut top surface 122 of the retainer and prevent disengagement of the members.

The suture clip is configured and dimensioned to accommodate all of the commonly available suture sizes. Typically, the lengthwise extension 111a may be from about 0.20 to about 0.30 inches, and width 111b may be from about 0.10 to about 0.20 inches. The retainer member 120 may be from about 0.30 to about 0.40 inches long and from about 0.10 to about 0.20 inches wide. The aperture 121 may be from about 0.20 to about 0.30 inches long and from about 0.05 to about 0.06 inches wide, according to the dimensions of legs 112 and 113. The side wall 121b and retainer 120 may be from about 0.25 to about 0.35 inches high. These dimensions are given by way of exemplification of preferred ranges and are not to be construed as limiting the scope of the present invention to the stated sizes.

The suture clip 100 is employed in accordance with the following method. The suture clip first and second members, 110 and 120, are initially separated. One or more suture threadlines 130 are positioned transversely over and across the legs 112 and 113 as shown in FIG. 1.

Next the first and second members are moved towards each other, the legs 112 and 113 being inserted into aperture 121 until snap fit engagement is completed and the first and second members 110 and 120 are locked together. The first and second members may be manually joined, or they may be joined by means of a suitable instrument.

Figure 3:
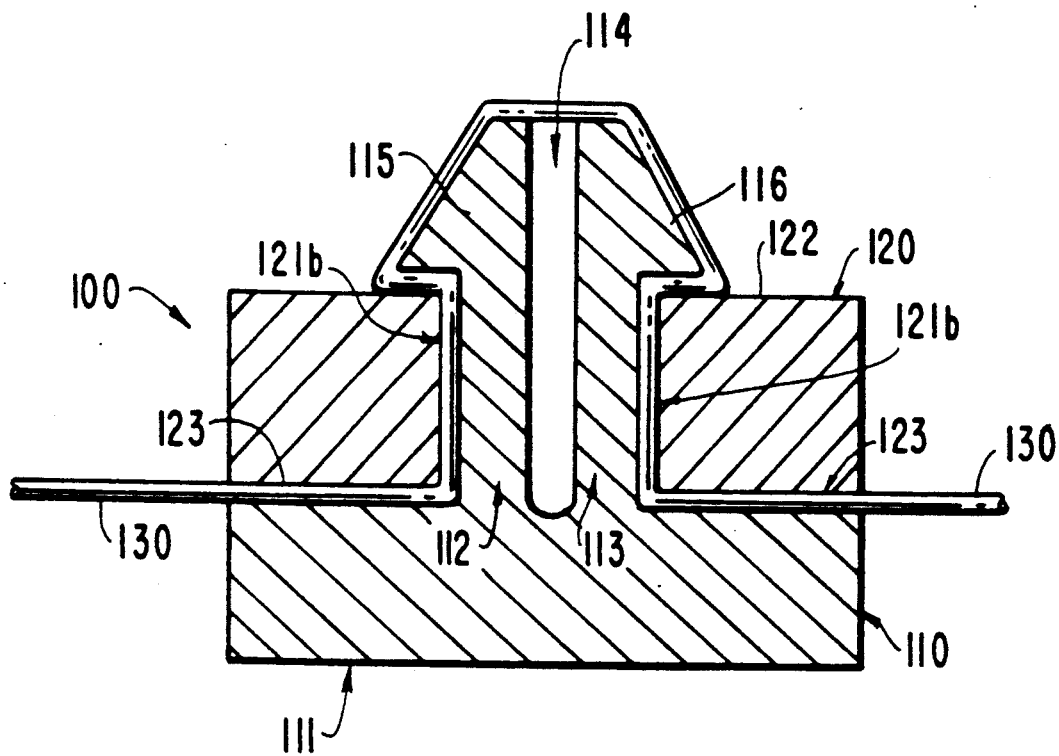
FIG. 3 is a sectional view showing a suture in conjunction with a closed clip of the present invention.

Once the suture clip 100 is assembled, the suture 130 is securely held in serpentine configuration as shown in FIG. 3. During use, the two legs 112 and 113 will deflect sufficiently to capture a range of suture sizes while the leg resilience biases the legs against the capture surface 121b to retain the suture with similar force regardless of suture size. Therefore, one size suture clip 100 will accommodate all of the typical suture sizes.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:
1. A suture fastening device which comprises:
a) a first member having a lengthwise extension defined by its longest side and including a base portion,
    first and second legs projecting from said base portion and extending lengthwise along the base portion,
    said first and second legs parallel to each other along the lengthwise direction of the base, and being resiliently biased toward a spaced apart position from each other and movable toward each other in response to force applied thereto; and
b) a second member having a lengthwise extension defined by its longest side, said second member having an aperture for receiving said first and second legs of said first member.

2. The suture fastening device of claim 1 wherein said first and second legs are substantially perpendicular to said base member.

3. The suture fastening device of claim 1 wherein said first and second legs each possess a camming surface and said second member possesses camming means for camming against said camming surfaces of said first and second legs to move said first and second legs toward each other.

4. The suture fastening device of claim 3 wherein said camming means of said second member is an edge defined by the conjunction of said aperture with a bottom surface of said second member.

5. The suture fastening device of claim 1 including means for joining said first and second members in snap-fit locking engagement.

6. The suture fastening device of claim 5 wherein said means for joining includes at least one barb extending from at least one of said first and second legs, said barb having an abutment surface for preventing disengagement of said first and second members after said first and second members have been engaged.

7. The suture fastening device of claim 1 wherein said first and second members are fabricated from a bioabsorbable material.

8. The suture fastening device of claim 7 wherein said bioabsorbable material comprises a material selected from the group consisting of polymers of glycolide, lactide, caprolactone, and 1,4-dioxanone.

9. The suture fastening device of claim 1 wherein said first and second legs are positioned side by side and parallel to each other in said direction of elongation parallel to the lengthwise extension of the first member.

10. A method for securing a suture, comprising:
a) providing a suture fastening device including a first member having a base portion, and first and second legs projecting from said base portion and extending lengthwise along the base portion, said first and second legs being resiliently biased toward a spaced apart position from each other and movable toward each other in response to force applied thereto, and a second member having an aperture for receiving said first and second legs of said first member;
b) positioning a suture transversely across both said first and second legs;
c) moving said second member and said first member into engagement with each other such that said first and second legs and a portion of said suture are received into said aperture.

11. The method of claim 10 wherein said first and second legs are substantially perpendicular to said base member.

12. The method of claim 10 wherein said first and second members are substantially parallel to each other.

13. The method of claim 10 wherein said first and second legs each possess a camming surface and said second member possesses camming means for camming against said camming surfaces of said first and second legs to move said first and second legs toward each other.

14. The suture fastening device of claim 13 wherein said camming means of said second member is an edge defined by the conjunction of said aperture with a bottom surface of said second member.

15. The method of claim 10 including means for joining said first and second members in snap-fit locking engagement.

16. The suture fastening device of claim 15 wherein said means for joining includes at least one barb extending from at least one of said first and second legs, said barb having an abutment surface for preventing disengagement of said first and second members after said first and second members habe been engaged.

17. A suture fastening device, which comprises:
a) a first member having a lengthwise extension defined by its longest side and including a base portion, first and second legs spaced apart from each other and projecting from said base portion, said first and second legs being resiliently biased to said spaced apart position and movable toward each other in response to a force applied thereto, and said first and second legs each having an inner side defining a gap therebetween, said gap having a longitudinal axis extending between first and second openings located at the ends of said longitudinal axis, the longitudinal axis of the gap being substantially parallel to the lengthwise extension of the first member; and
b) a second member having an aperture for receiving said first and second legs of said first member, said first and second members being relatively movable between an open position wherein said first and second members are relatively spaced apart from each other and a closed position wherein said first and second members are engaged.

18. The suture fastening device of claim 17 wherein said legs are movable toward each other in a direction transverse to the lengthwise extension of said first member when said second member is moved into engagement with said first member.

19. The suture fastening device of claim 18 wherein each of said first and second legs possesses a camming surface on a side of the leg opposite said inner facing side.

20. The suture fastening device of claim 17 wherein said first and second legs are elongated.

* * * * *